(12) United States Patent
Spaide et al.

(10) Patent No.: US 8,939,582 B1
(45) Date of Patent: Jan. 27, 2015

(54) OPTICAL COHERENCE TOMOGRAPHY WITH DYNAMIC FOCUS SWEEPING AND WINDOWED AVERAGING

(71) Applicant: Kabushiki Kaisha Topcon, Tokyo (JP)

(72) Inventors: Richard F. Spaide, New York, NY (US); Charles A. Reisman, Mamaroneck, NY (US); Zhenguo Wang, Fort Lee, NJ (US); Kinpui Chan, Ridgewood, NJ (US)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 13/940,899

(22) Filed: Jul. 12, 2013

(51) Int. Cl.
*A61B 3/14* (2006.01)
*A61B 3/10* (2006.01)
*A61B 3/00* (2006.01)

(52) U.S. Cl.
USPC .......................... 351/206; 351/205; 351/246

(58) Field of Classification Search
USPC .................................................. 351/200–246
See application file for complete search history.

(56) References Cited

U.S. PATENT DOCUMENTS

| | | | |
|---|---|---|---|
| 5,847,827 A | 12/1998 | Fercher | |
| 6,057,920 A | 5/2000 | Fercher et al. | |
| 2003/0128756 A1 | 7/2003 | Oktem | |
| 2008/0024767 A1 | 1/2008 | Seitz | |
| 2011/0299034 A1* | 12/2011 | Walsh et al. | 351/206 |
| 2012/0184846 A1* | 7/2012 | Izatt et al. | 600/425 |

FOREIGN PATENT DOCUMENTS

EP    2087308 B1    10/2012

OTHER PUBLICATIONS

Itakura, Hirotaka et al., "Observation of Posterior Precortical Vitreous Pocket Using Swept-Source Optical Coherence Tomography" In: Investigative Opthamalogy & Visual Science, May 2013, vol. 54, No. 5: pp. 3102-3107.
Holmes, Jon, Michelson Diagnostic Ltd "Theory & applications of multi-beam OCT" In: Proceedings Spiedigital Library; 2008; vol. 7139, 713908-1 through 7, May.
Huber, R. et al. "Three-dimensional and C-mode OCT imaging with a compact, frequency swept laser source at 1300 nm" In: Optics Express; 2005, vol. 13, No. 26, pp. 10523-10538, Jun.
Schmitt, Joseph "Optical Coherence Tomography (OCT): A Review" In: IEEE Journal of Selected Topics in Quantum Electronics; Jul./Aug. 2009; vol. 5; No. 4; pp. 1205-1215.
Du, Chixin et al. "Anterior Segment Biometry during Accommodation Imaged with Ultralong Scan Depth Optical Coherence Tomography" In: Opthalmology; 2012; vol. 119, No. 119; pp. 2479-2485, Jul.
Zhou, Chaunquing et al "Dual channel focus optical coherence tomography for imaging accommodation of the eye" In: NIH Public Access Author Manuscript; 2009; 17(11); pp. 8947-8955, Jul.
Shen, Meixiao et al. "Entire contact lens imaged in vivo and in vitro with spectral domain optical coherence tomography" In:NIH Public Access Author Manuscript; 2010; 36(2); pp. 73-76, Jun.
Shen, Meixiao et al. "SD-OCT With Prolonged Scan Depth for Imaging the Anterior Segment of the Eye" In: Ophthalmic Surgery, Laser & Imaging; 2010; vol. 41, No. 6; pp. S65-S69 Jun.

* cited by examiner

Primary Examiner — Mohammed Hasan
(74) Attorney, Agent, or Firm — Pearne & Gordon LLP

(57) ABSTRACT

During scan capture with an OCT imaging system, the focal plane position can be simultaneously shifted over at least a portion of an image range. As a result, a plurality of image frames respectively corresponding to various focal plane positions is acquired. The image frames can be combined to generate a composite image having suitable resolution throughout the image range, including regions associated with weak-intensity or low-reflectance features. Further, windowed averaging can be performed prior to generation of the composite image so that the composite image incorporates weights given to image data in focus.

25 Claims, 16 Drawing Sheets

OPTICAL COHERENCE TOMOGRAPHY WITH DYNAMIC FOCUS SWEEPING AND WINDOWED AVERAGING

BACKGROUND OF THE INVENTION

1. Field of the Invention

This application relates generally to optical coherence tomography (OCT) imaging methods and apparatus and, more specifically, to an OCT imaging method and apparatus utilizing dynamic focus and/or windowed averaging.

2. Description of Related Art

OCT is an imaging technique capable of acquiring subsurface images of a subject at micrometer resolutions. In ophthalmological applications, OCT is utilized to generate cross-sectional images of portions of an eye, including the posterior (e.g. retina) and/or anterior (e.g., cornea, crystalline lens, etc.) regions. While clinical applications have traditionally focused on the posterior region, there is growing interest in OCT imaging of the vitreous, the choroid, the sclera, the crystalline lens, and, essentially, all portions of the eye. For instance, the vitreous, and particularly the condition of the vitreous, can contribute to various blinding eye conditions such as retinal detachment, macular holes, and diabetic retinopathy. However, OCT signal intensity of the vitreous, the crystalline lens, and, often, the choroid and/or sclera is weak, i.e., close to a background noise level.

In clinical practice, commonly used OCT instruments utilize spectral domain technology, and thus have a high roll-off in sensitivity with depth. Accordingly, imaging wider expanses of the vitreous becomes difficult. With the emergence of swept source OCT, which has a lower roll-off in sensitivity with depth, imaging the vitreous is potentially easier. However, the illumination beam is constrained by the physics of how light is focused. For instance, a high numerical aperture system focuses light to a relatively smaller spot, but results in a higher cone angle for the beam of light. The higher cone angle in turn reduces a range over which the beam of light is at an acceptable diameter (i.e. provides suitable resolution). A lower numerical aperture system has a longer zone in which the beam is narrow, but the minimum diameter of the focused light beam is comparatively larger. Thus, lower numerical aperture systems typically have reduced transverse or lateral resolution than high numerical aperture systems.

Moreover, the dimensions of the beam of light lead to other effects. In the vitreous, for example, the reflective structures include collagen fibers and individual cells, each of which is very small. A larger illumination beam leads to reflections from these reflective, yet small, structures, but the same beam also illuminates surrounding areas that are potentially non-reflective. As a consequence, the total light reflected back to the OCT instrument is a small proportion of the light entering the eye. The total light used in diagnostic instruments is severely limited by the need to maintain safety limits and, therefore, cannot be increased to compensate for the inefficiencies of the illumination system.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, dynamic focus sweeping is utilized during an OCT scan to optimize imaging of low-reflectance structures including the vitreous, crystalline lens, choroid, sclera, cornea etc. With dynamic focus sweeping, a focal plane is adjusted. The adjustment to the focal plane can be continuous or discrete. The OCT scan, employing dynamic focus sweeping, generates a plurality of image frames respectively corresponding to focal plane positions of a set of focal plane positions. The image frames, of the plurality of image frames, can have disparate focal plane positions and, thus, provide high lateral resolution at different locations within the image range. The image frames of the plurality of image frames can be registered (i.e., aligned) to generate a composite image having suitable resolution throughout the image range, including regions associated with weak-intensity or low-reflectance features.

In another aspect, before generation of the composite image, the image frames, of the plurality of image frames, are registered and averaged. In the averaging process, a window can be positioned with respect to focal properties. By way of example, for an image frame, a corresponding window is positioned such that a center of the window corresponds to a focal plane position for the image frame. For each window, weightings are applied to intensity values. For instance, intensity values of the image frame can be weighted on a row-by-row basis in accordance with weights specified by the window. A sum total of row-by-row intensity weightings, from one or more windows, is maintained. This sum total enables generation of a composite, averaged image frame with physically accurate pixel intensity levels.

In a further aspect, the final composite image, generated from dynamic focus sweeping with or without windowed averaging, can be subjected to display-related processing operations to optimize display of the image.

These and other embodiments are described in more detail below.

BRIEF DESCRIPTION OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
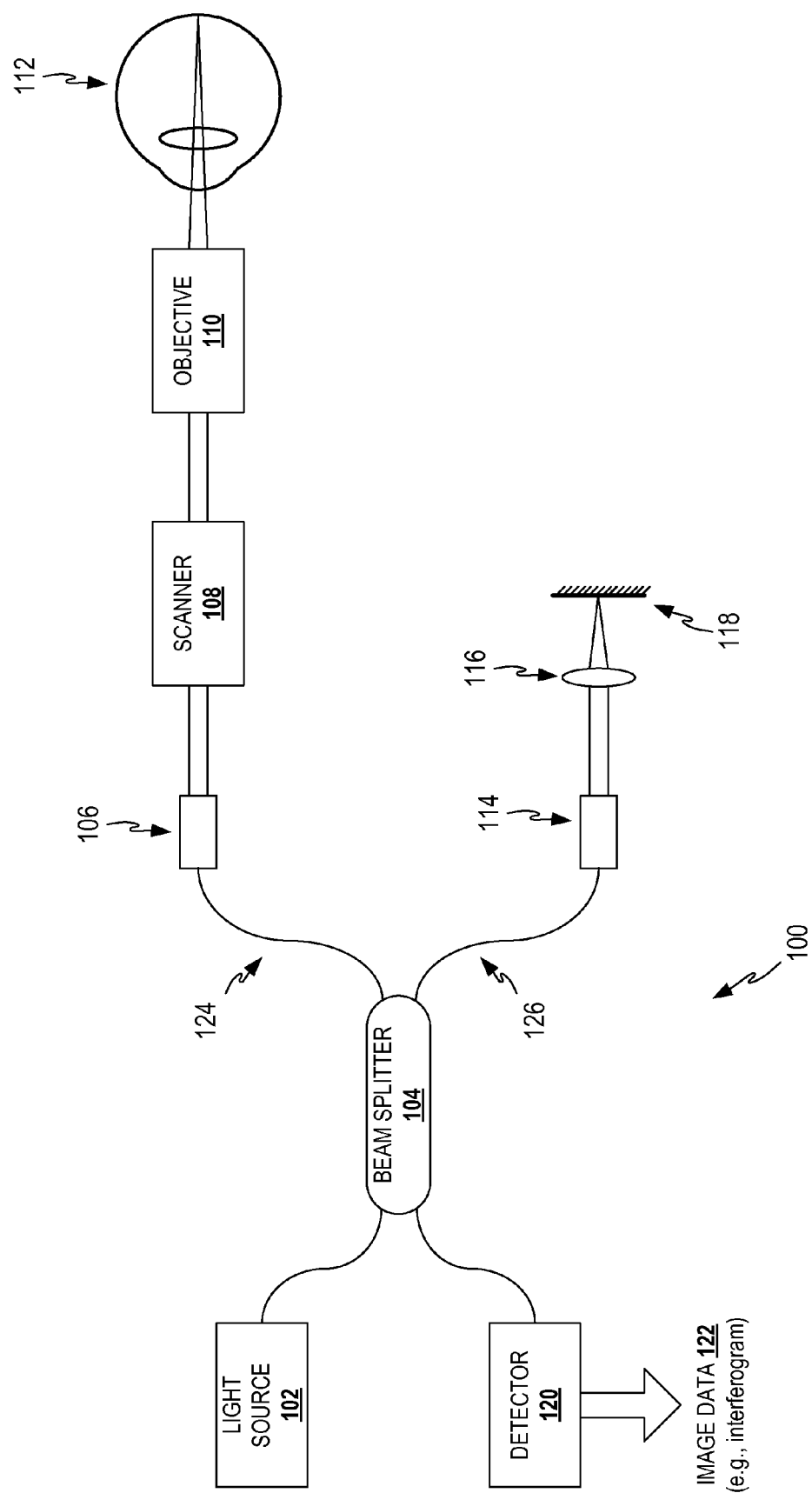
FIG. 1 illustrates a schematic diagram of an exemplary, non-limiting OCT imaging system with dynamic focus sweeping.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

According to one of more aspects described herein, during scan capture with an OCT imaging system, the focal plane position can be simultaneously shifted over at least a portion of an image range. As a result, a plurality of image frames respectively corresponding to various focal plane positions is acquired. The image frames can be combined to generate a composite image having suitable resolution throughout the image range, including regions associated with weak-intensity or low-reflectance features. Further, windowed averaging can be performed prior to generation of the composite image so that the composite image incorporates weights given to image data in focus.

In one embodiment, an optical coherence tomography (OCT) imaging system is described herein. The OCT imaging system includes an optical sub-system for capturing OCT scan data of a subject. The optical sub-system can include an objective lens for transmitting a scanning beam from a light source to the subject. The objective lens can be configurable such that a focal plane position relative to the subject is adjustable. The OCT imaging system can also include a control apparatus for controlling the capturing of OCT scan data by the optical sub-system, for configuring the objective lens to adjust the focal plane position relative to the subject, and for processing the OCT scan data to generate at least one OCT image.

According to one example, the control apparatus can include at least one display and at least one processor. The at least one processor can be configured to implement an optical scan control for providing control signals to the optical sub-system, an image processor for converting the OCT scan data to the at least one OCT image, and a display processor for outputting the at least one OCT image to the display. The control apparatus controls the optical sub-system such that the OCT scan data comprises a plurality of scan captures respectively associated with a plurality of focal plane positions. Further, the control apparatus is further configured to convert the plurality of scan captures into a plurality of OCT images, generate a windowed average of the plurality of OCT images, and generate a composite OCT image based on the windowed average. For instance, to generate the windowed average, the control apparatus weights respective pixel intensities of respective OCT images, of the plurality of OCT images, based on respective focal plane positions associated with the respective OCT images. The pixel intensities are weighted based at least in part on a distance from the focal plane position.

According to another example, the control apparatus controls the optical sub-system to generate a preliminary image of the subject utilized to adjust the optical sub-system for scanning the subject. For instance, the control apparatus detects an anchor point within an image range associated with the preliminary image of the subject and adjusts a reference mirror of the optical sub-system so that a position of the anchor point within the image range is at a predetermined location. In a specific example, the subject can an eye and the anchor point can be one of a retina, a sclera, a choroid, a cornea, or a crystalline lens of the eye. Prior to capturing the OCT scan data, the control apparatus configures the objective lens so that the focal plane position is at a predetermined location within an image range. The control apparatus controls the optical sub-system to perform a plurality of scan captures and, simultaneously, configures the objective lens to shift the focal plane position through a plurality of positions within an image range.

According to another embodiment, a method of focus sweeping with an OCT imaging system is described. The method can include scanning, by the OCT imaging system, a subject to acquire a plurality of scan captures and adjusting a focal plane position within the subject to a plurality of focal plane positions within an image range of the OCT imaging system. In an example, adjusting of the focal plane position occurs simultaneously with scanning of the subject so that, for each focal plane position, of the plurality of focal plane positions, one or more scan captures are acquired.

According to another example, adjusting the focal plane position can include sliding the focal plane position from one edge of the image range to the other. The slide of the focal plane positions can be continuous or, alternatively, the plurality of focal plane positions can correspond to a set of discrete features within the subject.

In yet another example, the method can also include aligning a reference mirror of the OCT imaging system to shift the image range to a different position relative to the subject and rescanning the subject to acquire a second plurality of scan captures associated with the different position of the image range while simultaneously adjusting the focal plane position within the image range.

Still further, the method can include converting the plurality of scan captures to a plurality of image frames, registering each image frame, of the plurality of image frames, to a template frame, applying weights to each image frame in accordance with the focal plane position, of the plurality of focal plane positions, associated with the image, and averaging the weighted image frames to generate a composite image.

In yet another embodiment, an OCT imaging system is described herein that includes an optical sub-system for capturing OCT scan data of a subject, wherein the OCT scan data comprises a plurality of scan captures respectively associated with a plurality of focal plane positions. The OCT imaging system further includes an image processor for converting the OCT scan data to a plurality of OCT images, for performing a windowed average over the plurality of OCT images based on the plurality of focal plane positions, and for outputting a composite image based on the windowed average.

According to an example, the optical sub-system is configured to transmit a plurality of light beams, respectively having disparate depths of focus, to the subject. The disparate depths of focus correspond to the plurality of focal plane positions. In another example, the optical sub-system includes an objective lens for transmitting a scanning beam from a light source to the subject. The objective lens can be configurable such that a focal plane position relative to the subject is adjustable to the plurality of focal plane positions.

According to another embodiment, a method for generating a composite image of a subject from OCT scan data is provided. The method can include acquiring, by an OCT imaging system, a plurality of image frames respectively associated with a plurality of focal plane positions, performing windowed averaging on the plurality of image frames, wherein the windowed averaging weights the plurality of image frames based on respective focal plane positions, and generating the composite image from a result of the windowed averaging. In an example, performing windowed averaging can include, for an image frame of the plurality of image frames respectively associated with a focal plane position, weighting the image frame with a weighting image generated based on the focal plane position and summing the image frame, as weighted with the weighting image, with other image frames similarly weighted.

In another example, the method can further include registering the image frame to a template frame to generate transform parameters and transforming the weighting image and the image frame with the transform parameters prior to the weighting of the image frame. Still further, the method can include summing the weighting image with other weighting images associated with other focal plane positions. Accordingly, generating the composite image comprises computing a quotient between summed, weighted image frames and summed weighting images.

According to yet another embodiment, a method for OCT imaging is described. The method can include scanning, by an OCT imaging system, a subject to acquire a plurality image frames. The method can further include controlling the OCT imaging system during the scanning to change a focal plane position within the subject successively through a set of focal plane positions within an image range of the OCT imaging system. In an example, controlling the OCT imaging system is simultaneous with scanning the subject such that at least one image frame is acquired at each focal plane position of the set of focal plane positions. The method can also include weighting respective image frames, of the plurality of image frames, with respective weighting images generated based on respective focal plane positions at which the respective image frames are acquired, generating a composite image based on the plurality of image frames, as weighted, and the respective weighting images, and outputting the composite image for display.

FIG. 1 illustrates an exemplary, non-limiting OCT imaging system 100 in which one or more aspects described herein can be implemented. FIG. 1 is a simplified depiction of an OCT imaging system intended to provide a general structural overview and does not necessarily represent a complete implementation of an imaging system. For example, optical elements such as polarization controllers, additional beam splitters, other light paths, etc., are omitted for clarity. For instance, the schematic illustration of FIG. 1 is intended to generally encompass various OCT implementations such as, but not limited to, time-domain OCT, spectral-domain OCT, and/or swept-source OCT since the techniques described and claimed herein can be utilized in connection with substantially any form of OCT imaging.

In general, OCT operates according to the same basic principles as ultrasound but utilizes light as a medium whereas ultrasound utilizes sound. That is, OCT images the subject by irradiating the subject with light and measuring a time delay and intensity of reflected light. However, light is much faster than sound. So, unlike the time delay in an ultrasound echo, the time delay of the reflected light is not directly measured. Instead, OCT utilizes low-coherence interferometry to detect time differences corresponding to distances between structures of the subject. Particularly, a low-coherence broadband light source is split into a sample portion and a reference portion. The reference portion travels a path toward a reference (i.e., a reference mirror) while the sample portion is directed towards the subject (e.g., an eye and, specifically, the retina). When a distance traveled by the sample portion and a corresponding reflection off the subject is within a coherence length of a distance traveled by the reference portion and its corresponding reflection, an interference pattern is generated. The interference pattern indicates an intensity of light at a certain depth of the subject, which in turn, facilitates generating image data pertaining to the subject.

To derive intensity information at varying depths of the subject, several different techniques can be utilized. In one technique, referred to as time-domain OCT, the travel distance of the reference portion is modulated to scan different depths. For example, the reference mirror can be oscillated to change the travel distance. Other techniques, which can be collectively referred to as frequency-domain OCT, do not require alterations to the reference portion. In these techniques, various wavelengths can be encoded, spatially or temporally for example, where different detected frequencies of interference signal correspond to different depths within the subject. A Fourier analysis on a received signal that represents reflected intensities at different frequencies generates the intensities reflected at different depths at a point of the subject.

According to one example of a frequency-domain OCT technique (commonly referred to as Fourier-domain or spectral-domain OCT), a reference interference pattern is dispersed into individual wavelength components by a grating or other such dispersive means. Conceptually, an array of photodetectors, each sensitive to a specific range of wavelengths, simultaneously detects respective intensities of the frequency components corresponding to different depths at a scanned point of the subject. In conventional practice, however, typically a charge couple device (CCD) or complimentary metal-oxide-semiconductor (CMOS) line camera or spectrometer is utilized and the grating physically separates the different wavelengths of light. In another example, referred to as swept-source OCT, a tunable light source is utilized to scan over different wavelengths. The intensities at each scanned wavelength can be collected and transformed by a Fourier analysis to generate an intensity profile that details intensities at various depths.

For OCT imaging, and as utilized herein, various properties can be defined as follows:

$$\text{Image Range: } Z_{im} = \frac{\lambda^2}{4\Delta\lambda}$$

$$\text{Depth of Focus: } Z_f = \frac{8\lambda}{\pi}\left(\frac{f}{\Phi}\right)^2$$

$$\text{Beam Waist Diameter: } X_f = \frac{4\lambda}{\pi}\left(\frac{f}{\Phi}\right)$$

In the formulas above, $\lambda$ represents a wavelength, $\Delta\lambda$ represents a spectral sampling width, f is a focal length, and $\Phi$ represents a beam diameter. Conceptually, the image range represents an axial distance over which scan data is captured (i.e., the z-axis dimension of the sample volume). The depth of focus represents a range over which a beam of light has a suitable diameter for OCT imaging. A spot size (i.e. a cross-sectional radius) of the beam of light is at a minimum size at one position within the depth of focus. That position is referred to as a beam waist and the minimum size associated with that position is referred to as the beam waist diameter. The beam waist diameter can be a measure of lateral or transverse resolution, wherein a smaller beam waist diameter generally corresponds to a higher transverse resolution. The depth of focus is generally centered on a focal plane, which is an optical plane perpendicular to the z-axis and passes through the beam waist. While described as a "plane", the focal plane can be a curved surface due to various aberrations.

As can be observed from the formulas above, the image range and the depth of focus are independent of each other for OCT imaging. However, the depth of focus $Z_f$ and the beam waist diameter $X_f$ are both dependent on a numerical aperture. The numerical aperture is proportional to $\Phi/f$, and, as seen from the above formulas, has a greater impact on the depth of focus than on the beam waist diameter (or transverse resolution).

Figure 15:
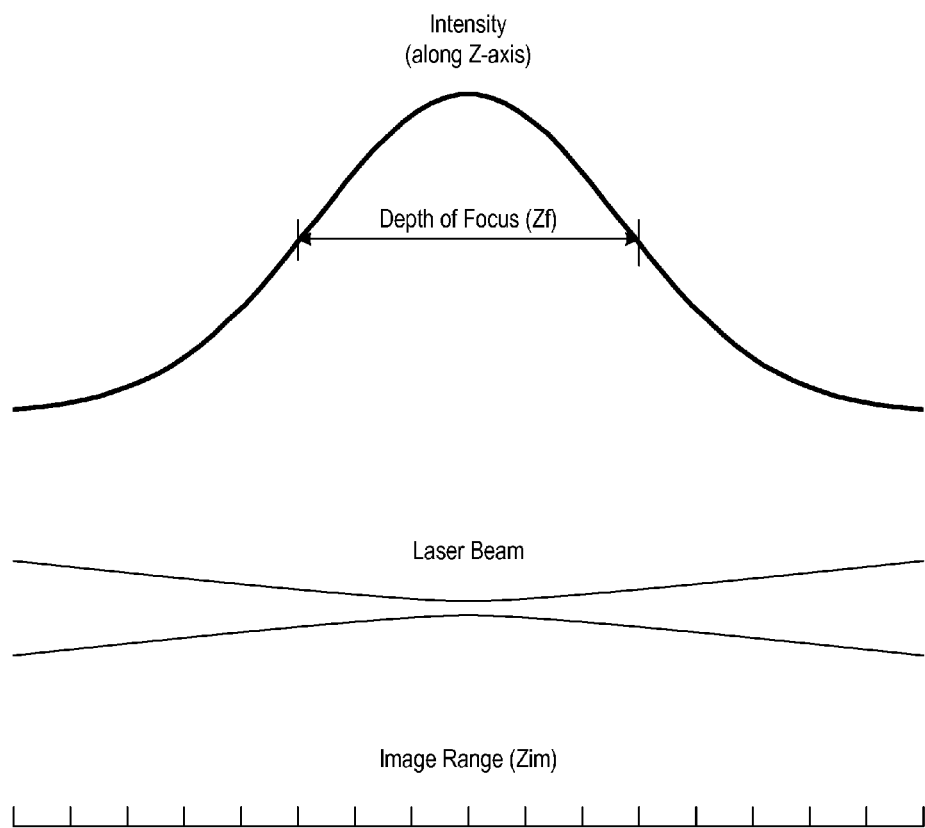
FIG. 15 illustrates optical characteristics associated with an OCT image.

For a typical ophthalmic OCT imaging system, the depth of focus $Z_f$ is approximately 1 millimeter while the image range $Z_{im}$ is approximately 3 millimeters. FIG. 15 illustrates these characteristics associated with an OCT image over the image range. The intensity, along the Z-axis over the image range substantially corresponds to a Gaussian shape centered on the focal plane. As shown, the depth of focus largely corresponds to the portion of the image range having greater intensity and excludes the lower intensity portions of the image range. The Gaussian shape of the intensity follows from the shape or diameter of the laser beam as shown in FIG. 15. At the focal plane, the laser beam narrows and becomes more intense. Accordingly, reflections off tissues or other portions of the eye around the focal plane will also have greater intensity and lateral resolution will be effectively higher (i.e., improved).

Conventional OCT systems generally have a depth of focus that roughly corresponds to an image range. This introduces a non-uniformity of several decibels in terms of signal-to-noise ratio (SNR). This non-uniformity, in turn, adversely affects the performance of OCT as a high sensitivity imaging modality for weak intensity structures such as the vitreous, choroid, cornea, crystalline lens, and/or sclera. Moreover, matching the depth of focus to the image range negatively impacts a transverse resolution. As technological advances in OCT imaging systems are trending towards increased image range, this strategy of matching depth of focus and image range will greatly degrade transverse resolution. Further, when regions of weak intensity are located away from the focal plane, which is typically aligned with the retina for posterior ophthalmic imaging and the cornea, iris, or crystalline lens for anterior ophthalmic imaging, the capability to image such low intensity features is compromised by depth of focus characteristics of the lens system. Accordingly, imaging weak intensity features is difficult to achieve simultaneously with a high quality retinal image with conventional OCT imaging systems.

In an aspect, the OCT imaging system 100 in FIG. 1 is configured to generate cross-sectional images of portions of an eye 112 including the retina, sclera, choroid, vitreous, cornea, iris, crystalline lens, and/or the entire eye 112. Such images are generated, generally, by impinging light from light source 102 onto the portions of the eye 112 and observing reflected light. Light source 102 can be a low-coherence broadband in the case of spectral-domain OCT or a tunable laser in the case of swept-source OCT. Light emitted from light source 102 is split by an optical adaptor such as a beam splitter 104 into two portions: a sample portion 124 that travels toward the eye 112, and a reference portion 126 that travels along a path toward a reference reflector. As shown in FIG. 1, the reference portion 126 can include a fiber optic cable leading to a collimator 114, which transmits the light from light source 102 to an optical element, such as lens 116, for focusing onto a reference mirror 118. Similarly, the sample portion 124 can follow a fiber optic cable to a collimator 106, which transmits light to a scanner 108. Scanner 108 is configured to direct or scan the light over various points of a surface of the eye 112. In particular, scanner 108 enables a two-dimensional (2D) scan of a focal plane established within the eye 112 by an objective 110. The objective 110, as described in greater detail below, enables a focal plane for the sample portion 124 to be adjusted to substantially any depth of the eye 112.

According to the principles of OCT, when a distance traveled by the sample portion and a corresponding reflection off the subject is within a coherence length of a distance traveled by the reference portion and its corresponding reflection, an interference pattern is generated. The interference pattern is detected by detector 120 and output as image data 122, which can be an interferogram. The interference pattern encodes intensity information for portions of the eye 112 which are scanned, which in turn, facilitates generating displayable images of the eye 112. The image data 122 can be provided to an image processor (not shown), which is described later.

Figure 2:
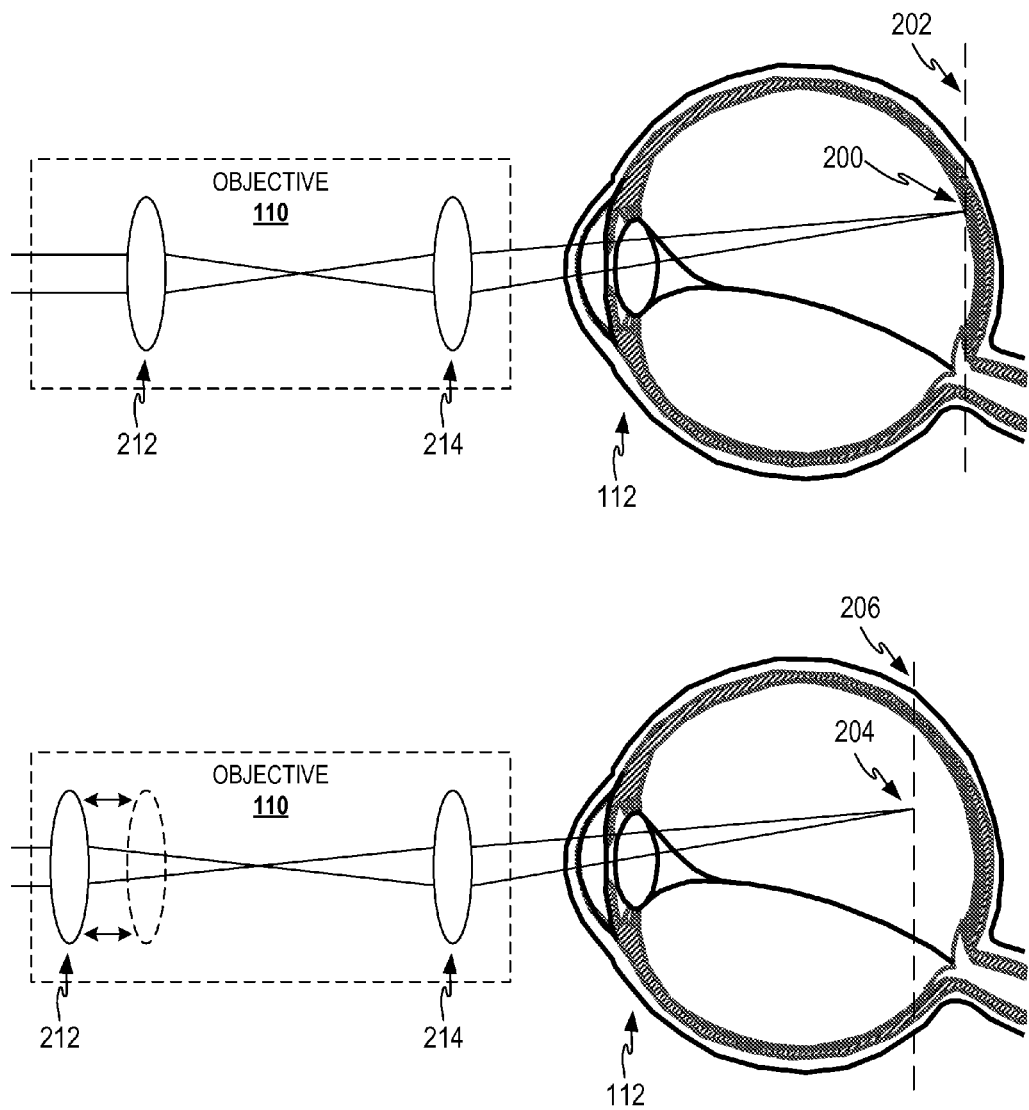
FIG. 2 is a diagram of an exemplary, non-limiting embodiment for an objective for use with an OCT imaging system to enable dynamic focus sweeping.

During a scan capture executed by system 100, objective 110 is adjusted so as to slide the focal plane to different positions within the eye 112. This dynamic focus sweeping facilitates generating an image across an entire imaging space in a composite image that includes features having weak intensities (e.g., vitreous, choroid, sclera, etc.) that would otherwise be missed with conventional OCT imaging. Turning to FIG. 2, one exemplary embodiment for objective 110 is illustrated. In FIG. 2, objective 110 includes a set of lenses, including lenses 212 and 214, which operate to adjust a focal plane within the eye 112. As shown in FIG. 2, the lenses 212 and 214 can be positioned relative to each other in a first state so that a resultant focal plane is a first focal plane 202 corresponding to a retina 200 of the eye 112. At least one of the lenses 212 and 214 is movable such that the lenses 212 and 214 can be transitioned to a second state having different relative positioning. In the second state, the focal plane is a second focal plane 206 corresponding to vitreous 204 of the eye 112.

Figure 3:
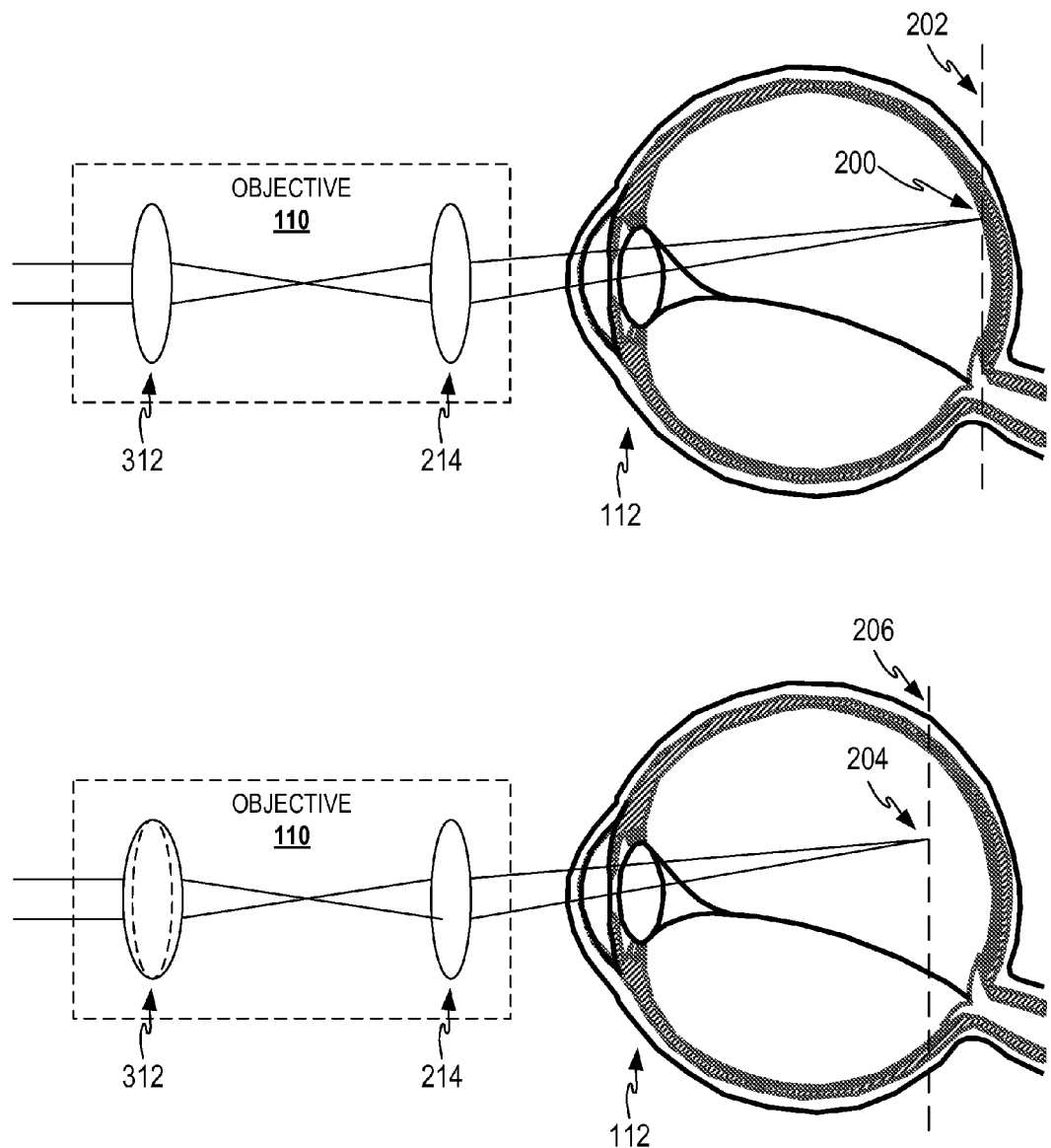
FIG. 3 is a diagram of an exemplary, non-limiting embodiment for an objective for use with an OCT imaging system to enable dynamic focus sweeping.

In an alternative embodiment, shown in FIG. 3, the objective 110 can include lens 214, which is the same as in FIG. 2 and a tunable lens 312. The tunable lens enables the focal plane to be changed from the first focal plane 202 to the second focal plane 206, for example, without a physical translation of a lens as depicted in FIG. 2. It is to be appreciated, however, that the embodiments of FIGS. 2 and 3 can be used in conjunction with each other. That is, it is to be appreciated that objective 110 can include one or more tunable lenses and one or more translatable lenses that are respectively controlled to enable sweeping of the focal plane throughout the eye 112.

Moreover, FIGS. 2 and 3 illustrate examples with two focal states. However, it is to be appreciated that more than two focal states can be achieved with the objective 110. Indeed, the objective 110 can be configured into a plurality of focal states corresponding to a plurality of focal plane positions within an image range of the OCT imaging system 100. The plurality of focal plane positions, according to an aspect, can include a set of discrete focal plane position in the image range. Alternatively, the plurality of focal plane positions can be substantially continuous over the image range, subject to a stepping size of a stepping motor, for example.

Further, a cuboid prism oriented at a small angle can be employed, in place of or in conjunction with, the objective 110 described above. The cuboid prism is constructed so, for each internal reflection, a portion of light is emitted. Accordingly, multiple beams of light are transmitted to the eye 112, each beam having a different depth of focus. In addition to the above techniques, it is to be appreciation that other techniques can be employed to transmit multiple beams of light, either simultaneously or consecutively, wherein the multiple beams of light have different depths of focus. Unless explicitly stated otherwise, image processing (i.e., windowed averaging) and/or display processing techniques described herein are intended to be applicable to OCT imaging systems that provide image data acquired from disparate focal depths, regardless of the manner in which the focal depth is controlled.

Figure 4:
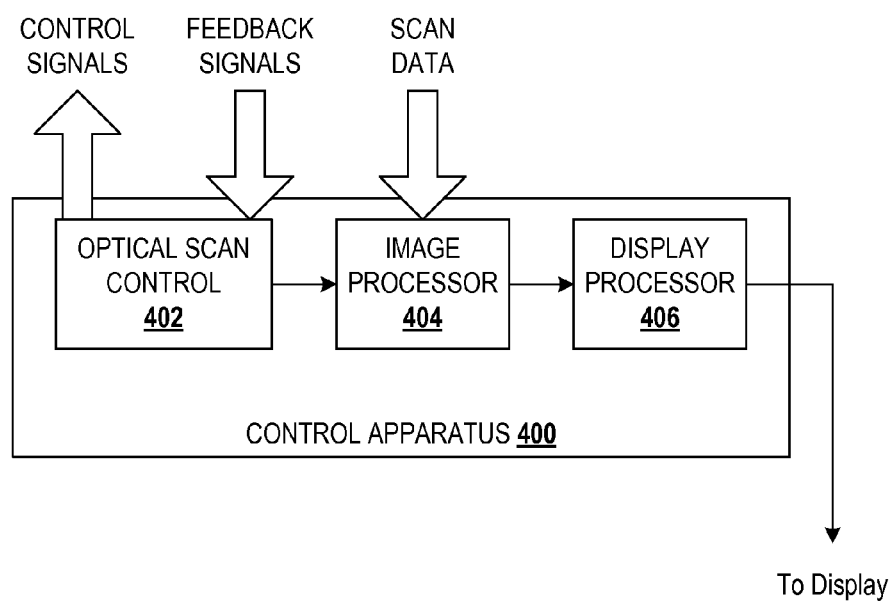
FIG. 4 is a block diagram of an exemplary, non-limiting control apparatus for an OCT imaging system according to one or more aspects of various embodiments herein.

As described above, the OCT imaging system 100 performs a scan of the eye 112 and outputs one or more interferograms (or A-lines), i.e., image data 122. FIG. 4 illustrates an exemplary, non-limiting control apparatus 400 that controls operation of the OCT imaging system 100 and processes scan data obtained therefrom. According to one example, control apparatus 400 can be implemented with a computing device, similar to the exemplary computing device described later, having one or more displays, one or more processors (distributed or co-located), non-transitory computer-readable media, user interface devices, and/or various communication interfaces.

As shown in FIG. 4, the control apparatus 400 includes an optical scan control 402 configured to provide control signals to OCT imaging system 100. The control signals can include signals to start/stop light source 102, to adjust scanner 108, to adjust objective 110, etc. The optical scan control 402 can also receive feedback signals from the OCT imaging system 100. Such feedback signals can indicate respective states of the scanner 108, the objective 110 (i.e., focal information), and other components of the OCT imaging system 100. As described in greater detail below, some information contained in the feedback signals can be provided to an image processor 404 to facilitate processing of a plurality of image frames captured at various focal plane positions. The image processor 404 obtains scan data, i.e., interferograms or image data 122, from the OCT imaging system 100 and, optionally, focal information, included in the feedback signals, from the optical scan control 402. According to an aspect, the scan data comprise a plurality of image frames captured at varying focal plane positions within an image range. It is to be appreciated that the plurality image frames can each be captured with different focal plane positions, that more than one image frame can captured with particular focal plane position, or one image frame can be captured over more than one focal plane position. The image processor 404 generates a composite image from the plurality of image frames. The composite image can be provided to a display processor 406 for additional, display-oriented processing before output to a display.

Figure 5:
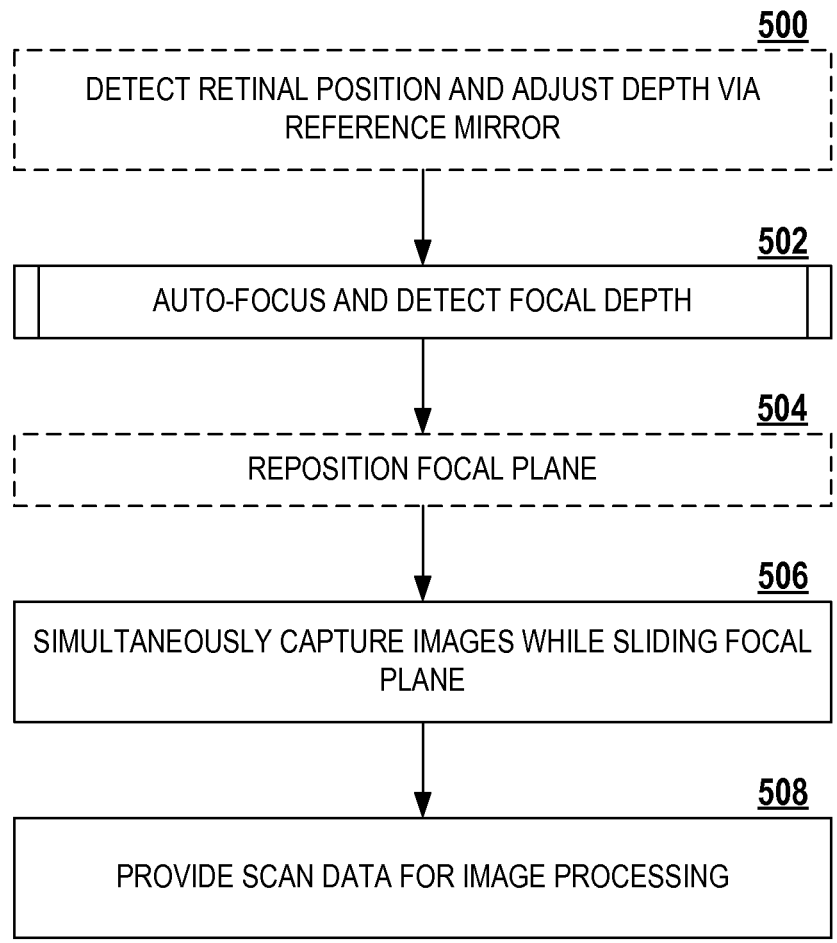
FIG. 5 is a flow diagram of an exemplary, non-limiting embodiment for OCT scanning with dynamic focus sweeping.

Turning to FIG. 5, illustrated is an exemplary, non-limiting process for performing an OCT scan with dynamic focus sweeping. This process can be carried out, for example, by system 100 described above, in connection with control apparatus 400 and, particularly, optic scan control 402, in order to generate scan data that corresponds to scan captures at multiple focal plane positions.

Figure 10:
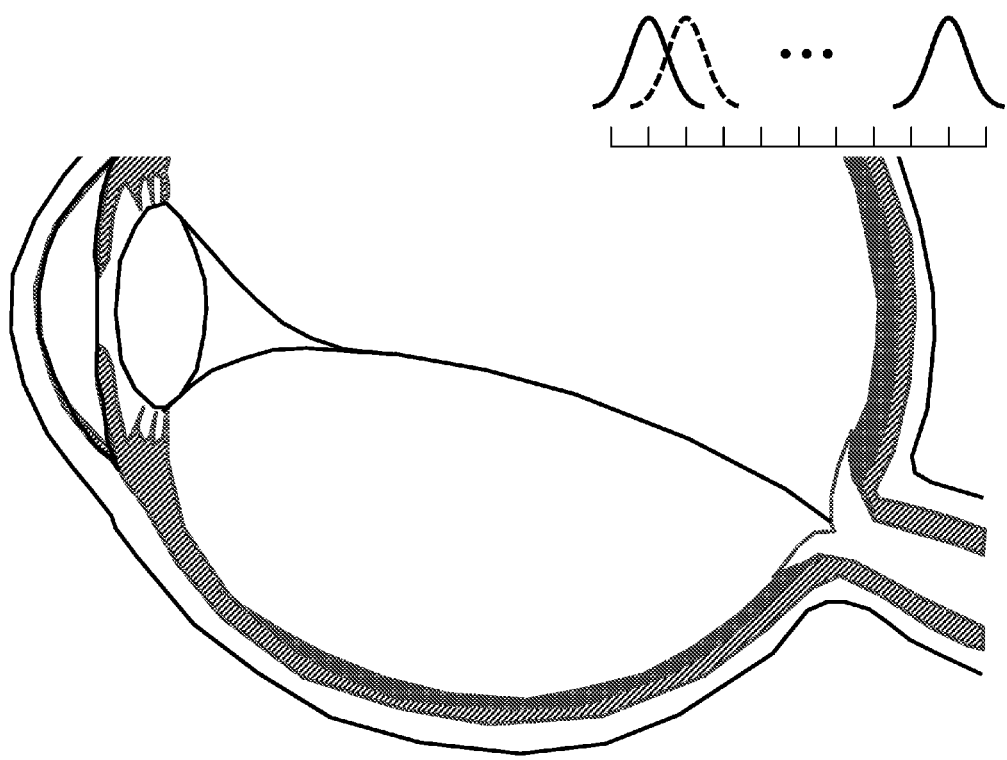
FIGS. 10-11 illustrate focus sweeping and windowed averaging, in terms of optical characteristics of OCT images, relative to an eye.
Figure 11:
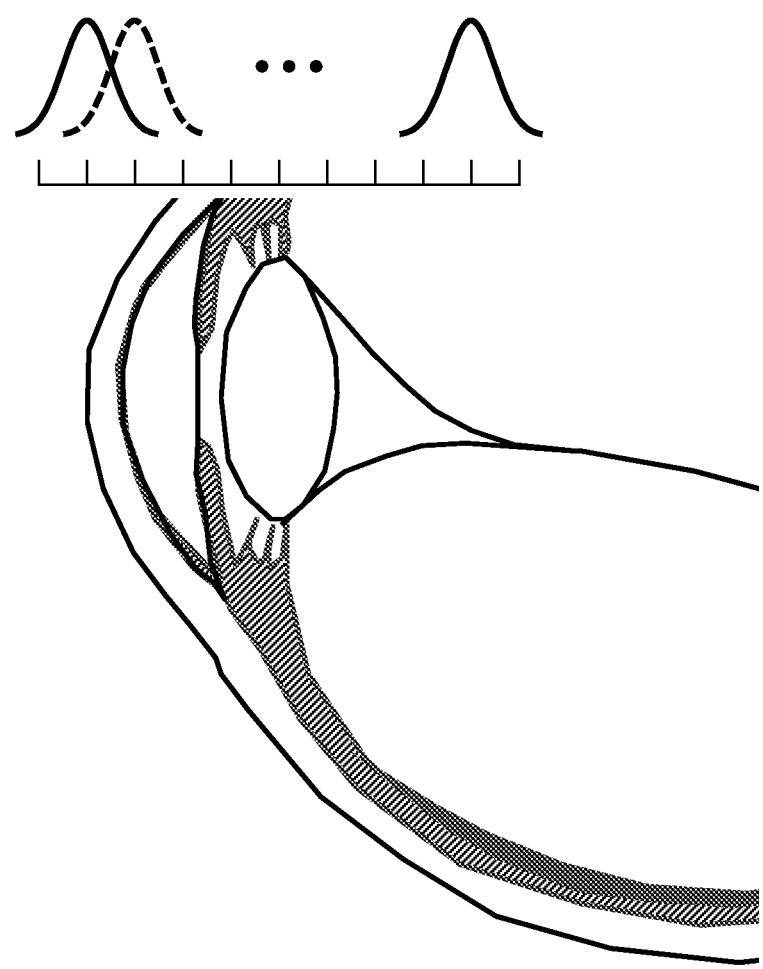

At 500, an optional process to detect an anchor point and adjust a depth via a reference mirror occurs. That is, a position of the anchor point within an image range is determined. Depending on the type of imaging desired, the anchor point can be the retina for posterior ophthalmic imaging or one of the cornea, iris, or crystalline lens for anterior ophthalmic imaging. The control apparatus 400 can utilize image processor 404 to determine the position of the anchor point in real-time or near real-time. The position of the reference mirror 118 can be adjusted, by control signals from the control apparatus 400, so that the position of anchor point relative to the image range is precisely set as desired. For example, with posterior ophthalmic imaging, the retinal position can be near an edge of the image range (e.g., in a bottom half of the image as displayed) so that a majority of the image range encompasses the vitreous. In contrast, as another example, for anterior imaging, the position of the crystalline lens (or cornea) can be near an edge of the image range corresponding to a top half as displayed. By way of illustration, the optional step at 500 can establish the position of the image range relative to the retina as shown in FIG. 10, the cornea as shown in FIG. 11, or essentially any other feature of the eye.

At 502, auto-focus and detection of a focal plane is performed. In an example, this process results in the focal plane being aligned with the position of the anchor point in the image range. This can occur via live-monitoring of the underlying tissue and via either a manual or automated procedure. As a manual process, a user can adjust the focal plane via a user interface while observing a live image. Via the user interface, the user can notify the control apparatus 400 when the focal plane and the anchor point are aligned. As an automated process, for instance, image signal strength is measured or an image quality indicator is determined while fine adjustments to the focal plane are made. Alignment between the focal plane and the position of the anchor point is achieved when the image signal strength, or the image quality score, is maximized. The focal plane position that maximizes the image signal strength or image quality indicator typically occurs, approximately, when the depth of focus includes the image feature of greatest mean intensity over a depth corresponding to the depth of focus. For instance, the image feature of greatest mean intensity can be the center of the retina (posterior imaging) or the cornea (anterior imaging). The depth of this particular feature can be estimated within the image range via standard image processing operations. For example, one technique to determine the depth of this image feature involves maximizing an integrated signal in the axial direction within a window having a width approximately equivalent to the depth of focus. For practical purposes, when the image signal strength or image quality indicator is maximized, the focal plane position can be determined to be a mean depth, calculated over all A-lines, of the feature corresponding to the maximum integrated signal strength using the selected window.

After alignment, the focal plane can be optionally repositioned to a predetermined known location at 504. In one example, the predetermined known location can be an extent of the image range. The repositioning can be achieved by considering one or more of the position of the anchor point determined at 500, the focal plane position as determined at 502, the image range, and focal characteristics as predetermined from optics of the OCT imaging system 100.

At 506, a plurality of images is sequentially captured, over a period of time, while simultaneously sliding the position of focal plane within the image range. The focal plane position is adjusted so that, at different times during the scan capture, the focal plane is at various depths of the eye. For example, with posterior imaging, the focal plane position can be adjusted so that the focal plane corresponds to the retina, the vitreous, and other depths within the eye at different times during the scan capture. The focal plane adjustment, in one example, can be a continuous linear adjustment such that the focal plane position is continuously and linearly moved correspondingly to image capture. For instance, the focal plane position can be initially at one extent of the image range and slides to the other extent of the image range along a linear profile. In another example, the focal plane adjustment can be continuous, but non-linear. In yet another example, discrete focal plane adjustments can be made, where the focal plane is positioned at particular depths (e.g., center of choroid, center of retina, center of crystalline lens, center of cornea etc.) and multiple scan captures are collected at each focal plane position. Further, it is to be appreciated that real-time (or near real-time) image analysis can be performed, with the help of image processor 404 for example, to facilitate the focal plane adjustments, whether continuous or discrete. Such image analysis can compensate for eye motion to ensure the focal plane is correctly adjusted to a desired position.

Figure 6:
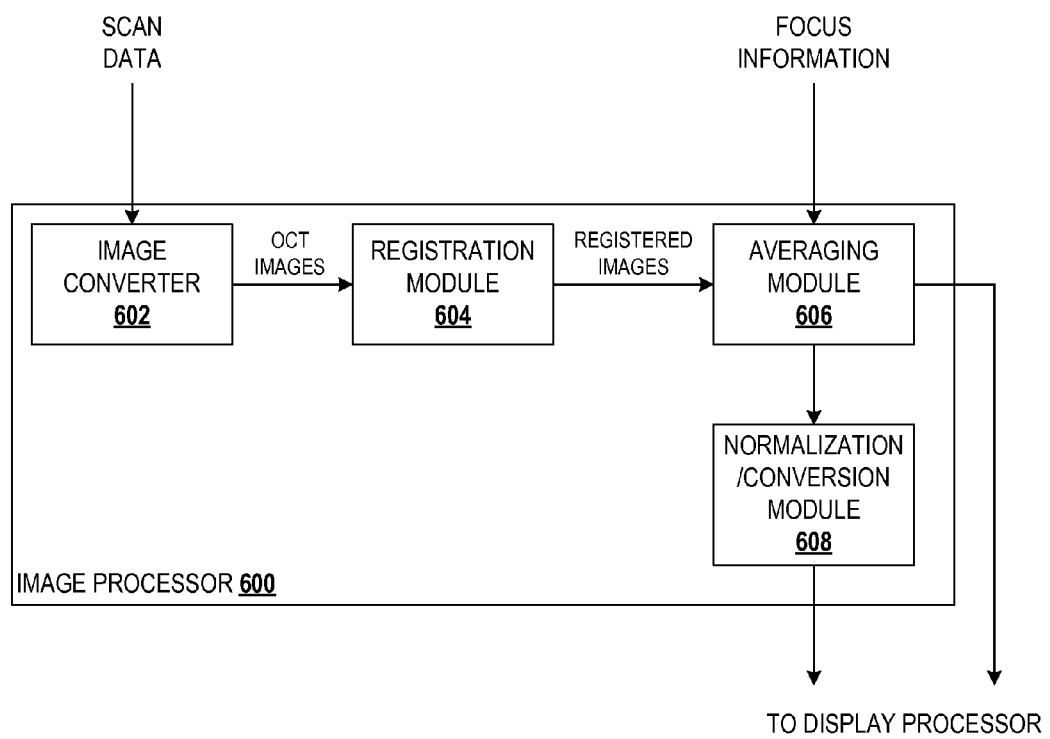
FIG. 6 illustrates a block diagram of an exemplary, non-limiting image processor for an OCT imaging system according to one or more aspects of various embodiments herein.

At the conclusion of the scan capture, the scan data is provided for image processing at 508. It is to be appreciated, that as utilized herein, the scan data acquired as described above can include a plurality of image frames. Each image frame is associated with a focal plane position, from a set of focal plane position, such that the image frame is captured while the focal plane is aligned at the associated focal plane position. FIG. 6 illustrates an exemplary, non-limiting image processor 600 according to one or more aspects. Image processor 600, for example, provides one exemplary embodiment for image processor 404 described above. As shown in FIG. 6, image processor 600 includes an image converter 602 that converts scan data, e.g., interferogram data, to OCT images that provide intensity information. The image converter 602 provides the OCT images to a registration module 604 for co-registration. In an aspect, the scan data includes a plurality of image frames captured from various focal plane positions. These image frames are registered together to a common template image or to some other selected image (i.e., first captured image, library image, previously generated composite image, etc.). The registered images are provided to an averaging module 606 that performs a row-by-row windowed averaging process. By way of example, intensity values in the images frames are weighted according to windows. The windows are centered at focal planes utilized during the scan capture. The positions of the focal planes and, accordingly, the positions of the windows within the image range can be determined from the focal information provided by the optical scan control 402. For each window, intensity values are weighted on a row-by-row basis, where a row corresponds to a specific depth within a depth of focus profile. Weighted intensity values for a given row are summed across all windows in which the given row is included. The summed, weighted intensity values for all rows are utilized to generate a composite image which can be output from the averaging module 606 to display processor 406 for further processing before display. Optionally, the composite image can be provided to a normalization/conversion module 608 to undergo normalization and/or data conversion to facilitate storage, display, or other desired, downstream processing.

Figure 7:
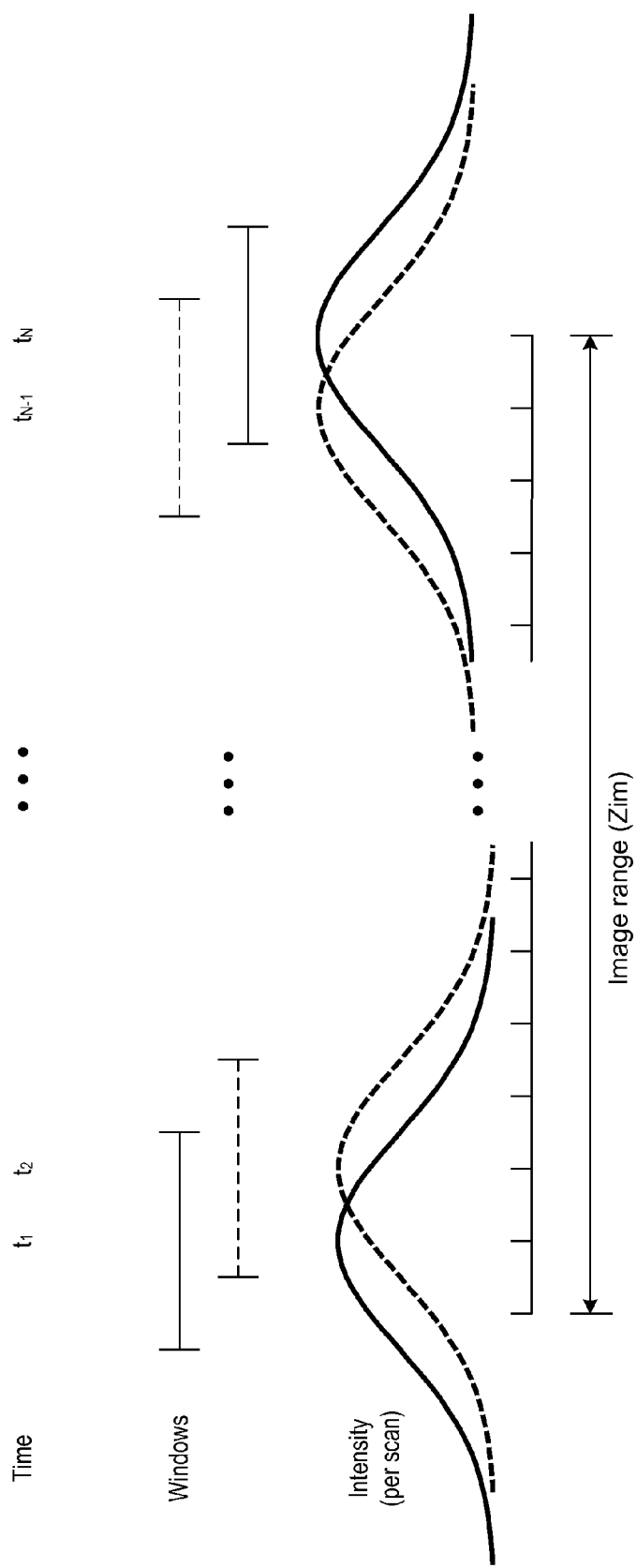
FIG. 7 illustrates an exemplary, non-limiting embodiment for focus sweeping and windowed averaging in terms of optical characteristics of OCT image.

To achieve simultaneous imaging of weak intensity features and high intensity features, focus sweeping, with or without windowed averaging, is utilized in accordance with one embodiment described herein. Turning to FIG. 7, this technique is illustrated. As depicted in FIG. 7, various scans are captured successively from time $t_1$ to $t_N$. For each scan, the focal plane can be shifted to a different position along the image range. Accordingly, for each scan, corresponding Gaussian intensity data is acquired as shown in FIG. 7 centered on the respective focal plane for the respective scan capture. It is to be appreciated that the Gaussian intensity curves illustrated in FIG. 7 do not represent absolute intensity values. Rather, the intensity curves, for each scan, correspond to degree at which an actual intensity value for a structure located at the corresponding position of the image range can be measured. In other words, better SNR and higher lateral resolution are achieved at position located near the focal plane of a scan and, thus, more accurate representation of relative physical intensity values can be achieved, regardless of whether the focal plane corresponds to a weak intensity feature (e.g., vitreous, sclera, crystalline lens) or a high intensity feature (e.g., retina, cornea). Moreover, it is to be appreciated that, while the Gaussian intensity curves are illustrated as extending beyond the image range, actual intensity values are not necessarily obtained for features outside the image range.

To generate a composite image from the plurality of scan captures, windowed averaging is employed. In FIG. 7, a respective window is shown for each scan capture, wherein each window is centered at the focal plane utilized for the corresponding scan capture. However, it is to be appreciated that each scan capture need not have a separate window associated therewith and that more than one scan capture can be associated with the same window. Moreover, the widths of the windows depicted in FIG. 7, are exemplary and it is to be appreciated that the widths can be smaller or greater than illustrated. In addition, it is to be appreciated that optical focal characteristics can vary over time (e.g., based on system controls) and/or by focal position. Accordingly, window characteristics can also vary correspondingly.

For a window, a weighting scheme is applied. The weights, in one example, can follow a Gaussian shape such that a maximum weight is applied to intensity values corresponding to a center of the window. According to this example, the window widths can be such that the Gaussian curve of weights substantially corresponds to the intensity curves for the scan capture, as described above. Thus, for a particular window, intensity values of features located away from the focal plane are discounted while intensity values of feature near the focal plane are favored. In another example, a rectangular window can be applied such that intensity values within the window are taken as is (e.g., weighting of 1) while intensity values outside the windows are zeroed out (e.g., weighting of 0). It is to be appreciated that the above weighting functions are exemplary and that the specific weighting function utilized for windowed averaging, as described herein, is largely arbitrary. For example, in addition to the functions described above, raised cosine or triangular windows can be utilized. In general, substantially any window shape or weighting function is suitable for use with the techniques described herein provided the selected window type achieves weighting rows of intensity values near a focus more than rows of intensity values far away from the focus.

Figure 8:
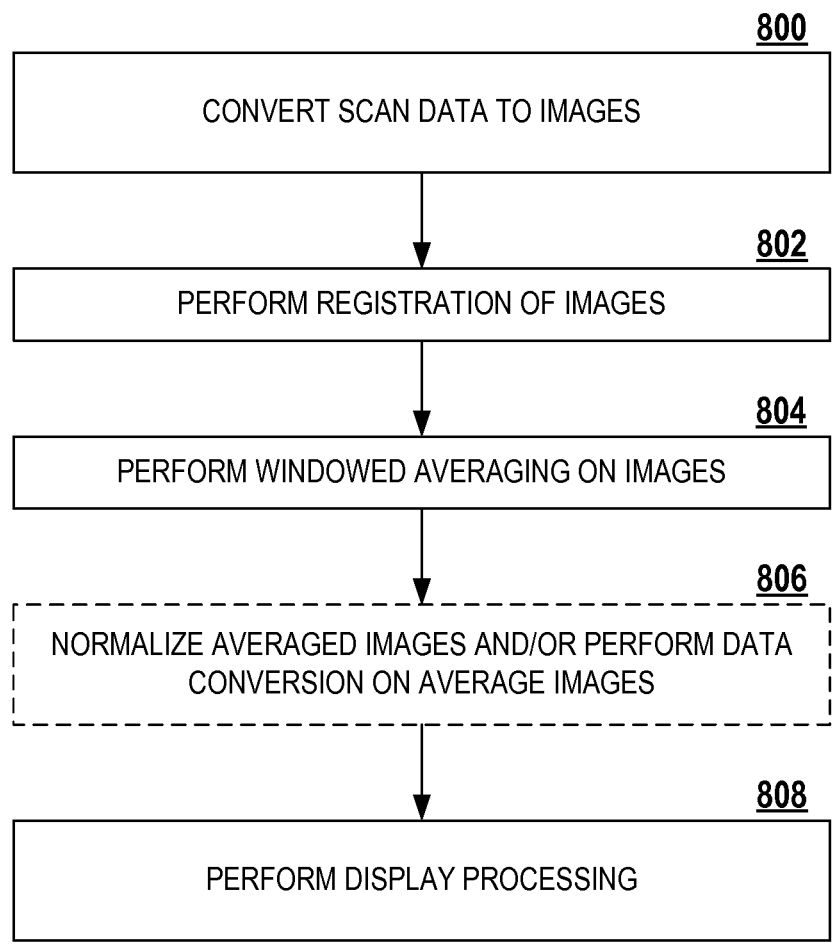
FIG. 8 is a flow diagram of an exemplary, non-limiting embodiment for windowed averaging of image frames.

FIG. 8 illustrates an exemplary, non-limiting method for windowed averaging of image frames. This method can be implemented, for example, by image processor 404 or 600. At 800, scan data is converted to a plurality of image frames. At 802, the image frames are co-registered. At 804, windowed averaging is performed. For each image frame, a window can be established in accordance with focal information corresponding to the image frame. The focal information can be acquired via a priori knowledge of the scan capture process, from explicitly communicated lens positions for each image frame as acquired by the scan capture process, and/or estimated based on a template frame. With this information, windows are established and applied to the registered image frames such that areas in focus are given higher weightings than areas out of focus (i.e., far from a depth of focus for a particular image frame). As described previously, the weightings can follow a Gaussian distribution or, alternatively, a rectangular window can be applied.

In accordance with one example, windows are established and centered for each focal plane position at which an image frame is captured. For each window, weightings are applied to intensity values within the window, on a row-by-row basis with a row corresponding to a specific depth within a depth of focus profile. For a row contained within multiple windows, respective weighted intensity values from the respective windows are summed. These summed, weighted intensity values across all windows are utilized to generate a composite image of the entire image range. For example, the summed, weighted intensity values can be divided by a total combined weighting corresponding to any given row to yield the composite image. At 806, the composite image can optionally undergo normalization and/or data conversion.

At 808, display processing is performed on the composite image. Display processing, according to an aspect, provides enhanced visualization of the composite image and, in particular, of the weaker intensity features such as the vitreous. Display-related processing operations can be performed include, but are not limited to, compression of an intensity signal range, gamma correction, and/or histogram equalization (e.g., adaptive histogram equalization, contrast-limited adaptive histogram equalization, etc.).

Figure 9:
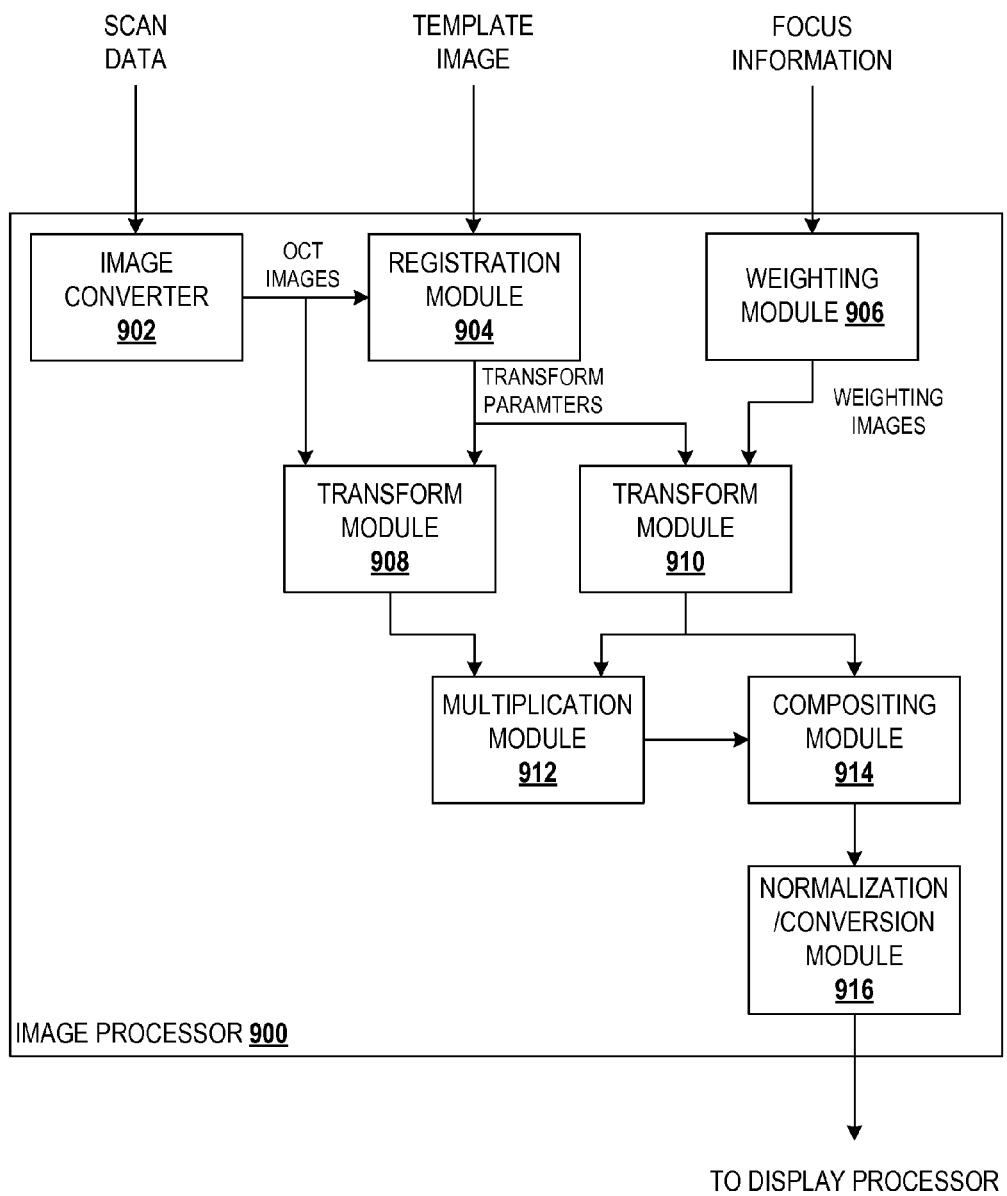
FIG. 9 illustrates a block diagram of an exemplary, non-limiting image processor for an OCT imaging system according to one or more aspects of various embodiments herein.

Turning now to FIG. 9, an exemplary, non-limiting image processor 900 according to one or more aspects is illustrated. Similar to image processor 600, image processor 900 provides another exemplary embodiment for image processor 404. As shown in FIG. 9, image processor 900 includes an image converter 902 that converts scan data, e.g., interferogram data, to OCT images that provide intensity information. The image converter 902 provides the OCT images to a registration module 904 for registration to a template image. The template image can be a library image, an image from a previous scan, a most recently generated composite image, a previously registered image frame from the same set, or the like. In other words, the template image can be updated over time based and/or different for each OCT image. For example, a first OCT image can be registered to the template frame which is a most recently generated composite image for the patient (or a library image). The first OCT image, as transformed according to the registration, can be the utilized as the template image for registration of a second OCT image, and so on. The registration module 904 generates transform parameters that specify an image transformation suitable to align the OCT images to the template space defined by the template image. The OCT images and the transform parameters are provided to a transform module 908 which transforms the OCT images in accordance with the parameters provided. While shown in aggregate in FIG. 9, it is to be appreciated that the OCT images can be individually registered by the registration module 904 to the template image such that respective transform parameters are generated for each image. Each image, in turn, is transformed by the transform module 908 with the respective transform parameters.

According to an aspect, windowed averaging is implemented by way of weighting images. A weighting module 906 generates one or more weighting images based on focus information, which indicates a focal plane position. As described above, the focal plane position can be known a priori, explicitly communicated by the optical sub-system, or estimated via image processing techniques. In one example, a weighting image provides, for each pixel, a weight to be applied to a corresponding pixel of an OCT image. The pixel weights are determined based on the focus information such that pixels at or near the focal plane position have higher weights than pixels farther away from the focal plane position.

The weighting images are provided to a transform module 910 for transformation in accordance with transform parameters from the registration module 904. In particular, for each OCT image, a corresponding weighting image can be generated based on the focal plane position associated with the OCT image. The transform parameters generated by the registration module 904 for the OCT image can be utilized, by transform module 910, to transform the corresponding weighting image. In an example, the registration module 904 can apply a registration technique such as a phase correlation technique, intensity-based registration, or feature-based registration.

After respective transformations by the transform modules 908 and 910, the OCT images are weighted according to the weighting images. For instance, a multiplication module 912 can perform pixel-by-pixel multiplication of an OCT image and a weighting image, thereby weighting each pixel (intensity value) of the OCT image by a weighting value specified by the weighting image. The weighted OCT images are provided to a compositing module 914 which generates a composite image from the plurality of weighted, OCT images. According to an example, the compositing module 914 sums the weighted OCT images and divides by a summation of weights across all weighting images. In particular, the compositing module 914 can generate the composite image according to the following:

$$I_C(x, z) = \frac{\sum_{n=1}^{N} I_n(x, z) \cdot w_n(x, z)}{\sum_{n=1}^{N} w_n(x, z)}$$

where N represents a total number of image frames, $I_n(x,z)$ refers to pixel intensity values in image frame n, $w_n(x,z)$ is a weighting image for image frame n and specifies pixel weights, and $I_C(x,z)$ refers to the pixel intensity values in the composite, averaged image.

The compositing module can output the composite image to display processor 406 for further processing before display. Optionally, the composite image can be provided to a normalization/conversion module 916 to undergo normalization and/or data conversion to facilitate storage, display, or other desired, downstream processing.

The above described process can be modified in a variety of ways. For instance, the weighting images and the OCT images can be multiplied prior to transformation according to the transform parameters. In another example, the independent weighting of OCT images through multiplication with weighting images can be avoided by applying the windowed weighting in the registration algorithm executed by the registration module 904. That is, the weights can be factored into the optimization process by which the transform parameters are derived.

Utilization of a weighting image facilitates modeling rotation, scaling, or skew induced by eye motion during scan capture. That is, by applying the transform parameters to the weighting image, computational errors resulting from eye motion are mitigated. However, it is to be appreciation that the transformation of the weighting image can be bypassed and would typical introduce only a minor degree of error. Noticeable errors can be observed during periods of notable eye motion in the axial direction (e.g., z-axis in the image space). However, this error can be mitigated through use of a weighting vector in place of the weighting image.

FIGS. 10 and 11 illustrate image ranges relative to an eye suitable for posterior ophthalmic imaging and anterior ophthalmic imaging, respectively. As depicted, by sliding the focal plane along the image range accurate intensity values for the different features (e.g., vitreous, retina, cornea, iris, crystalline lens, etc.) within the image range can be acquired. Through the use of windowed averaging described above, a composite image, from the plurality of scan captures, can be generated that represents physical reality.

Figure 12:
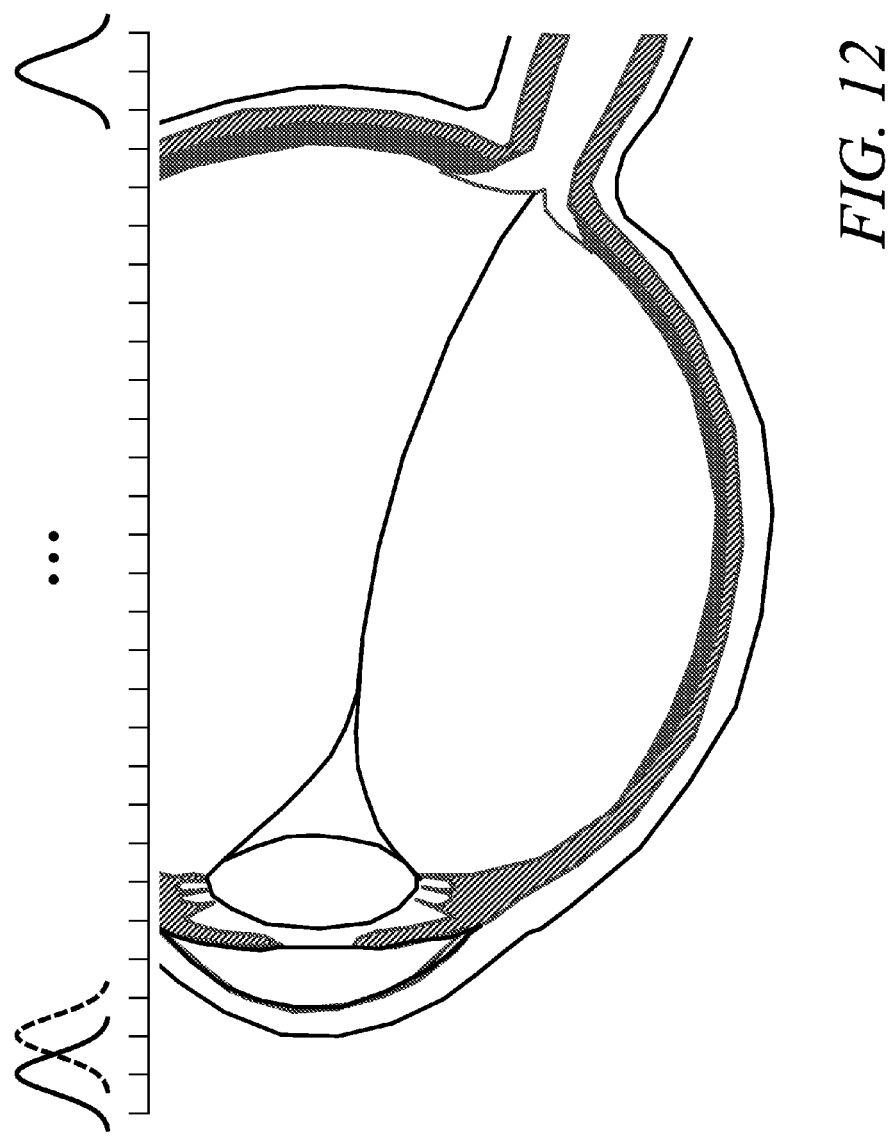
FIG. 12 illustrates an exemplary, non-limiting embodiment for utilizing dynamic focus sweeping in connection with long range OCT imaging.
Figure 13:
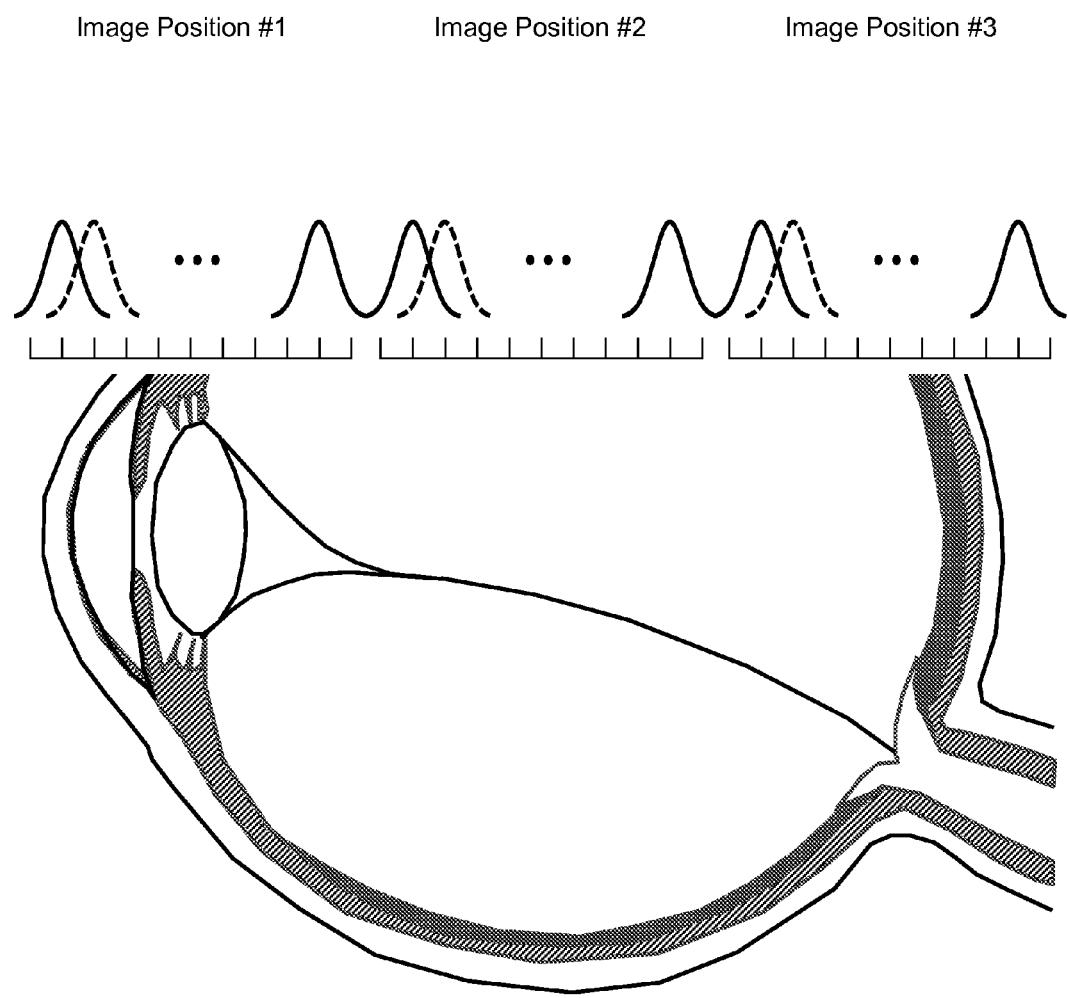
FIG. 13 illustrates an exemplary, non-limiting embodiment for long-range OCT imaging via multiple, short-range imaging utilizing dynamic focus sweeping.
Figure 14:
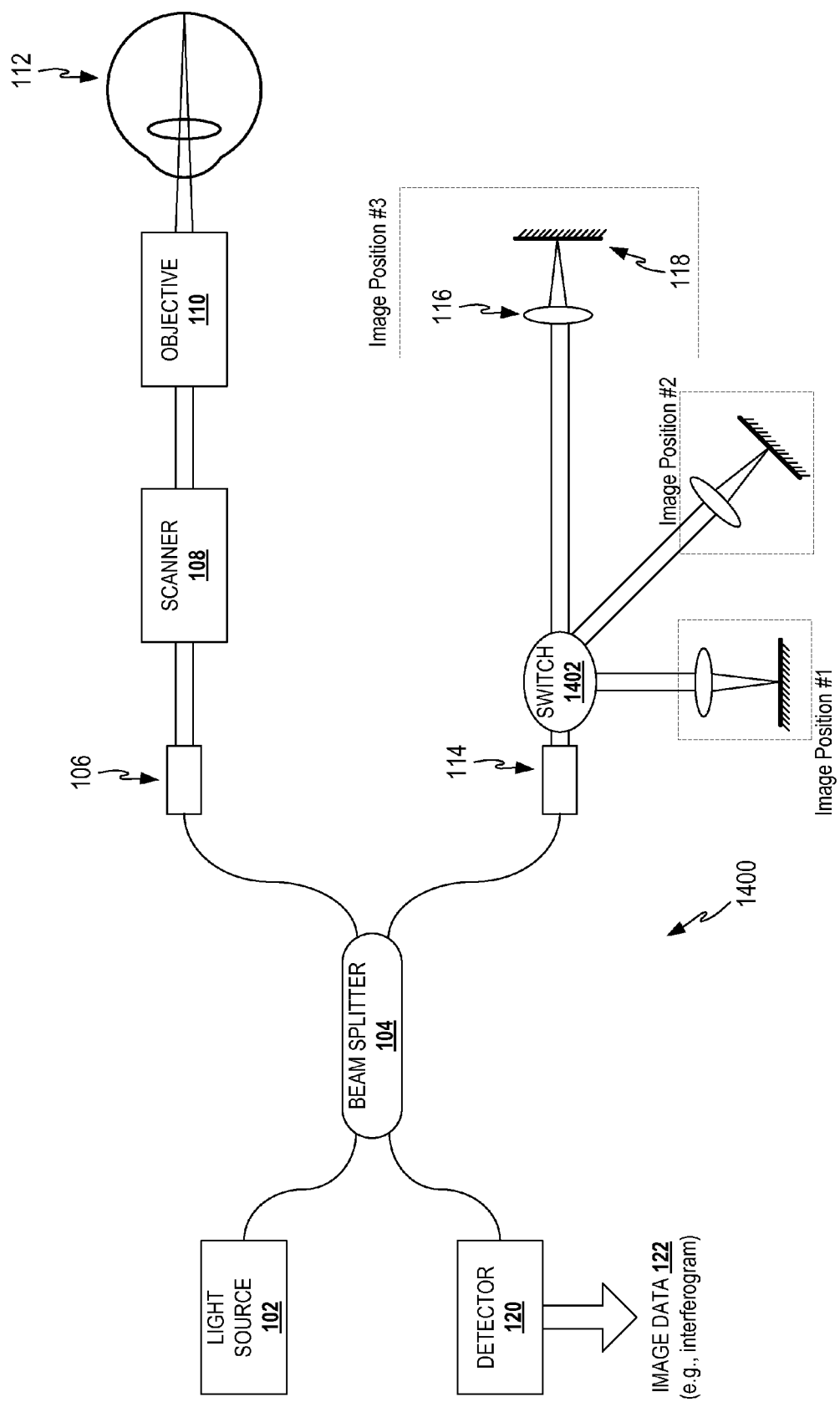
FIG. 14 illustrates a schematic diagram of exemplary, non-limiting OCT imaging systems with dynamic focus sweeping configured to perform long-range OCT imaging with multiple short-range scans in accordance with one embodiment.

With swept-source OCT, for example, an image range of several centimeters is achievable. As illustrated in FIG. 12, the dynamic focus sweeping and windowed averaging techniques can be applied with a long image range to generate a high quality, composite image of the entire eye including high-intensity features (retina, cornea) and low-intensity features (vitreous, crystalline lens). Moreover, as illustrated in FIG. 13, the high quality, composite image of the entire eye can be generated even with an OCT implementation having a conventional image range. As shown in FIG. 13, several shorter range images can be stitched together such that the shorter images, joined together, provide an image of the entire eye. As described above with respect to FIG. 5, the reference mirror 118 is positioned such that the image range includes the position of the anchor point (i.e., retinal position, position of the cornea, position of the crystalline lens, etc.). Through extension of this concept, several image positions can be utilized such that the corresponding image ranges are concatenated to form a long-range image comparable to that depicted in FIG. 12. FIG. 14 shows an OCT imaging system 1400 that includes a switch 1402 that enables the image position to be changed in order to capture images corresponding to different depths of the eye as shown in FIG. 13.

As described above, an inherent trade-off exists between image range and transverse resolution (or beam waist diameter) due to physical properties of light and optical properties associated with OCT imaging. More specifically, an increase in the transverse resolution (i.e. decreasing beam waist diameter), by, for example, increasing a numerical aperture, typically results in a decrease in the depth of focus. This shortening of the depth of focus can limit the effective image range. Similarly, increasing depth of focus (and correspondingly the image range), by decreasing the numerical aperture, typically reduces the transverse resolution (i.e., increases beam waist diameter). However, with the dynamic focus sweeping and windowed averaging techniques described herein, the effects of this trade-off can be mitigated. In other words, a high transverse resolution and also an improved SNR can be achieved over a long imaging range with the present invention.

For example, an OCT imaging system having a high numerical aperture typically generates high resolution image over a smaller depth of focus. Through dynamic focus sweeping, whereby the focal plane and, therefore, the depth of focus is panned across the image range, a high resolution image is captured over the entire image range. Moreover, several high resolution images captured over concatenated image ranges can further increase the effective image range.

Exemplary Computing Device

Figure 16:
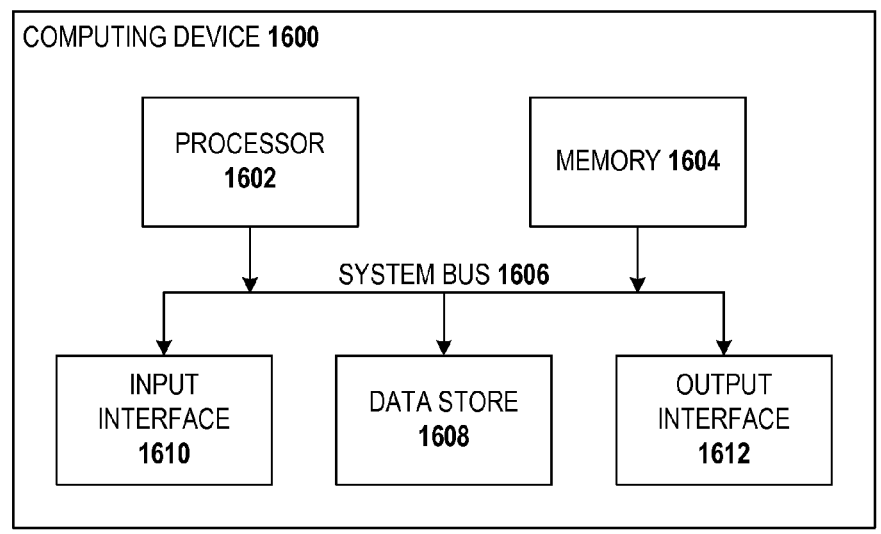
FIG. 16 illustrates a block diagram of an exemplary, non-limiting computing device or operating environment in which one or more aspects of various embodiments described herein can be implemented.

Referring now to FIG. 16, a high-level illustration of an exemplary computing device 1600 that can be used in accordance with the systems and methodologies disclosed herein is illustrated. The computing device 1600 includes at least one processor 1602 that executes instructions that are stored in a memory 1604. The instructions may be, for instance, instructions for implementing functionality described as being carried out by one or more components discussed above or instructions for implementing one or more of the methods described above. The processor 1602 may access the memory 1604 by way of a system bus 1606.

The computing device 1600 additionally includes a data store 1608 that is accessible by the processor 1602 by way of the system bus 1606. The computing device 1600 also includes an input interface 1610 that allows external devices to communicate with the computing device 1600. For instance, the input interface 1610 may be used to receive instructions from an external computer device, from a user, etc. The computing device 1600 also includes an output interface 1612 that interfaces the computing device 1600 with one or more external devices. For example, the computing device 1600 may display text, images, etc. by way of the output interface 1612. According to one exemplary embodiment, the output interface 1612 can be coupled to one or more displays (not shown).

Additionally, while illustrated as a single system, it is to be understood that the computing device 1600 may be a distributed system. Thus, for instance, several devices may be in communication by way of a network connection and may collectively perform tasks described as being performed by the computing device 1600.

Moreover, the acts described herein may be computer-executable instructions that can be implemented by one or more processors and/or stored on a computer-readable storage medium or media. The computer-executable instructions can include a routine, a sub-routine, programs, a thread of execution, and/or the like. Still further, results of acts of the methodologies can be stored in a computer-readable storage medium, displayed on a display device, and/or the like.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an"

as used in this application and the appended claims should generally be construed to mean "one or more" unless specified otherwise or clear from the context to be directed to a singular form.

Further, as used herein, the term "exemplary" is intended to mean "serving as an illustration or example of something."

Various functions described herein can be implemented in hardware, software, or any combination thereof. If implemented in software, the functions can be stored on or transmitted over as one or more instructions or code on a computer-readable medium. Computer-readable media includes both computer-readable storage media and communication media including any medium that facilitates transfer of a computer program from one place to another. A computer-readable storage media can be any available media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blue-ray disc (BD), where disks usually reproduce data magnetically and discs usually reproduce data optically with lasers. Further, a propagated signal is not included within the scope of computer-readable storage media. Also, a connection can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Illustrative embodiments have been described, hereinabove. It will be apparent to those skilled in the art that the above devices and methods may incorporate changes and modifications without departing from the general scope of the claimed subject matter. It is intended to include all such modifications and alterations within the scope of the claimed subject matter. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An optical coherence tomography (OCT) imaging system, comprising:
   an optical sub-system for capturing OCT scan data of a subject, the optical sub-system comprising an objective lens for transmitting a scanning beam from a light source to the subject, the objective lens being configurable such that a focal plane position relative to the subject is adjustable; and
   a control apparatus for controlling the capturing of OCT scan data by the optical sub-system, for configuring the objective lens to adjust the focal plane position relative to the subject, and for processing the OCT scan data to generate at least one OCT image such that for each focal plane position of a plurality of focal plane positions, the OCT scan data comprises one or more two-dimensional scan captures.

2. The OCT imaging system of claim 1, wherein the control apparatus comprising:
   at least one display; and
   at least one processor configured to implement:
     an optical scan control for providing control signals to the optical sub-system;
     an image processor for converting the OCT scan data to the at least one OCT image; and
     a display processor for outputting the at least one OCT image to the display.

3. The OCT imaging system of claim 1, wherein the control apparatus is further configured to convert the plurality of scan captures into a plurality of OCT images, generate a windowed average of the plurality of OCT images, and generate a composite OCT image based on the windowed average.

4. The OCT imaging system of claim 3, wherein, to generate the windowed average, the control apparatus weights respective pixel intensities of respective OCT images, of the plurality of OCT images, based on respective focal plane positions associated with the respective OCT images.

5. The OCT imaging system of claim 4, wherein pixel intensities are weighted based at least in part on a distance from the focal plane position.

6. The OCT imaging system of claim 1, wherein the control apparatus controls the optical sub-system to generate a preliminary image of the subject utilized to adjust the optical sub-system for scanning the subject, and
   wherein the control apparatus detects an anchor point within an image range associated with the preliminary image of the subject and adjusts a reference mirror of the optical sub-system so that a position of the anchor point within the image range is at a predetermined location.

7. The OCT imaging system of claim 6, wherein the subject is an eye and the anchor point is one of a retina, a sclera, a choroid, a cornea, or a crystalline lens of the eye.

8. The OCT imaging system of claim 1, wherein, prior to capturing the OCT scan data, the control apparatus configures the objective lens so that the focal plane position is at a predetermined location within an image range.

9. The OCT imaging system of claim 1, wherein the control apparatus controls the optical sub-system to perform a plurality of scan captures and, simultaneously, configures the objective lens to shift the focal plane position through a plurality of positions within an image range.

10. A method of focus sweeping with an OCT imaging system, comprising:
    scanning, by the OCT imaging system, a subject to acquire a plurality of two-dimensional scan captures; and
    adjusting a focal plane position within the subject to a plurality of focal plane positions within an image range of the OCT imaging system,
    wherein the adjusting of the focal plane position occurs simultaneously with the scanning of the subject so that, for each focal plane position, of the plurality of focal plane positions, one or more scan captures are acquired.

11. The method of claim 10, wherein adjusting the focal plane position further comprises sliding the focal plane position from one edge of the image range to the other.

12. The method of claim 11, wherein the sliding of the focal plane position is continuous.

13. The method of claim 10, wherein the plurality of focal plane positions correspond to a set of discrete features within the subject.

14. The method of claim 10, further comprising:
    aligning a reference mirror of the OCT imaging system to shift the image range to a different position relative to the subject; and rescanning the subject to acquire a second plurality of scan captures associated with the different position of the image range while simultaneously adjusting the focal plane position within the image range.

15. The method of claim 10, further comprising:
converting the plurality of scan captures to a plurality of image frames;
registering each image frame, of the plurality of image frames, to a template frame;
applying weights to each image frame in accordance with the focal plane position, of the plurality of focal plane positions, associated with the image; and
averaging the weighted image frames to generate a composite image.

16. An OCT imaging system, comprising:
an optical sub-system for capturing OCT scan data of a subject, wherein the OCT scan data comprises a plurality of scan captures respectively associated with a plurality of focal plane positions; and
an image processor for converting the OCT scan data to a plurality of OCT images, for performing a windowed average over the plurality of OCT images based on the plurality of focal plane positions, and for outputting a composite image based on the windowed average.

17. The OCT imaging system of claim 16, wherein the optical sub-system is configured to transmit a plurality of light beams, respectively having disparate depths of focus, to the subject,
wherein the disparate depths of focus correspond to the plurality of focal plane positions.

18. The OCT imaging system of claim 16, wherein the optical sub-system further comprises an objective lens for transmitting a scanning beam from a light source to the subject, the objective lens being configurable such that a focal plane position relative to the subject is adjustable to the plurality of focal plane positions.

19. A method for generating a composite image of a subject from OCT scan data, comprising:
acquiring, by an OCT imaging system, a plurality of image frames respectively associated with a plurality of focal plane positions;
performing windowed averaging on the plurality of image frames, wherein the windowed averaging weights the plurality of image frames based on respective focal plane positions; and
generating the composite image from a result of the windowed averaging.

20. The method of claim 19, wherein performing windowed averaging further comprises:
for an image frame of the plurality of image frames respectively associated with a focal plane position,
weighting the image frame with a weighting image generated based on the focal plane position; and
summing the image frame, as weighted with the weighting image, with other image frames similarly weighted.

21. The method of claim 20, further comprising registering the image frame to a template frame to generate transform parameters.

22. The method of claim 21, further comprising transforming the weighting image and the image frame with the transform parameters prior to the weighting of the image frame.

23. The method of claim 20, further comprising summing the weighting image with other weighting images associated with other focal plane positions.

24. The method of claim 23, wherein generating the composite image comprises computing a quotient between summed, weighted image frames and summed weighting images.

25. A method for OCT imaging, comprising:
scanning, by an OCT imaging system, a subject to acquire a plurality image frames;
controlling the OCT imaging system during the scanning to change a focal plane position within the subject successively through a set of focal plane positions within an image range of the OCT imaging system, wherein the controlling is simultaneous with the scanning such that at least one image frame is acquired at each focal plane position of the set of focal plane positions;
weighting respective image frames, of the plurality of image frames, with respective weighting images generated based on respective focal plane positions at which the respective image frames are acquired;
generating a composite image based on the plurality of image frames, as weighted, and the respective weighting images; and
outputting the composite image for display.

* * * * *

UNITED STATES PATENT AND TRADEMARK OFFICE
CERTIFICATE OF CORRECTION

PATENT NO. : 8,939,582 B1
APPLICATION NO. : 13/940899
DATED : January 27, 2015
INVENTOR(S) : Richard F. Spaide et al.

It is certified that error appears in the above-identified patent and that said Letters Patent is hereby corrected as shown below:

On the Title page, after (22) Filed: Jul. 12, 2013 please insert --(65) Prior Publication Data
US 2015/0015845 A1  January 15, 2015--

Signed and Sealed this
Seventh Day of July, 2015

Michelle K. Lee
*Director of the United States Patent and Trademark Office*